United States Patent [19]

Robertson et al.

[11] Patent Number: 4,701,193
[45] Date of Patent: Oct. 20, 1987

[54] SMOKE EVACUATOR SYSTEM FOR USE IN LASER SURGERY

[75] Inventors: Philip D. Robertson; Armando N. Solorzano, both of Colorado Springs, Colo.

[73] Assignee: Xanar, Inc., Colorado Springs, Colo.

[21] Appl. No.: 774,692

[22] Filed: Sep. 11, 1985

[51] Int. Cl.$^4$ ............................................ B01D 46/42
[52] U.S. Cl. .................................... 55/217; 55/274; 55/276; 55/385 R; 55/471
[58] Field of Search .................. 55/20, 163, 217, 274, 55/276, 467, 385 R, 385 A, 385 E, 468, 471

[56] References Cited

U.S. PATENT DOCUMENTS

| | | | |
|---|---|---|---|
| 3,027,865 | 4/1962 | Kautz et al. | 35/274 X |
| 3,665,681 | 5/1972 | Vitenko | 55/467 X |
| 3,950,155 | 4/1976 | Komiyama | 55/274 X |
| 4,078,390 | 3/1978 | Duvall | 55/20 X |
| 4,154,251 | 5/1979 | Doyel | 55/467 X |
| 4,163,650 | 8/1979 | Watson et al. | 55/467 X |
| 4,435,877 | 3/1984 | Berfield | 55/276 X |
| 4,468,236 | 8/1984 | Bauer | 55/20 |
| 4,504,286 | 3/1985 | Carlisle et al. | 55/20 |
| 4,557,108 | 10/1985 | Torimoto | 55/DIG. 30 X |

Primary Examiner—Charles Hart
Attorney, Agent, or Firm—Donal B. Tobin

[57] ABSTRACT

A smoke evacuator system for by-products of laser surgery including an inline construction of a motor and a filter assembly mounted on opposite sides of a mounting plate. The filter fits in a filter duct and the temperature of the flow between the filter and the vacuum chamber of the vacuum pump can be monitored to determine the clog condition of the filter. The system includes electronic circuitry to activate an alarm device to indicate to the user that the filter is clogged and further circuitry is provided to shutoff the motor after a long period of operation with a clogged filter to prevent damage to the system by overheating.

15 Claims, 6 Drawing Figures

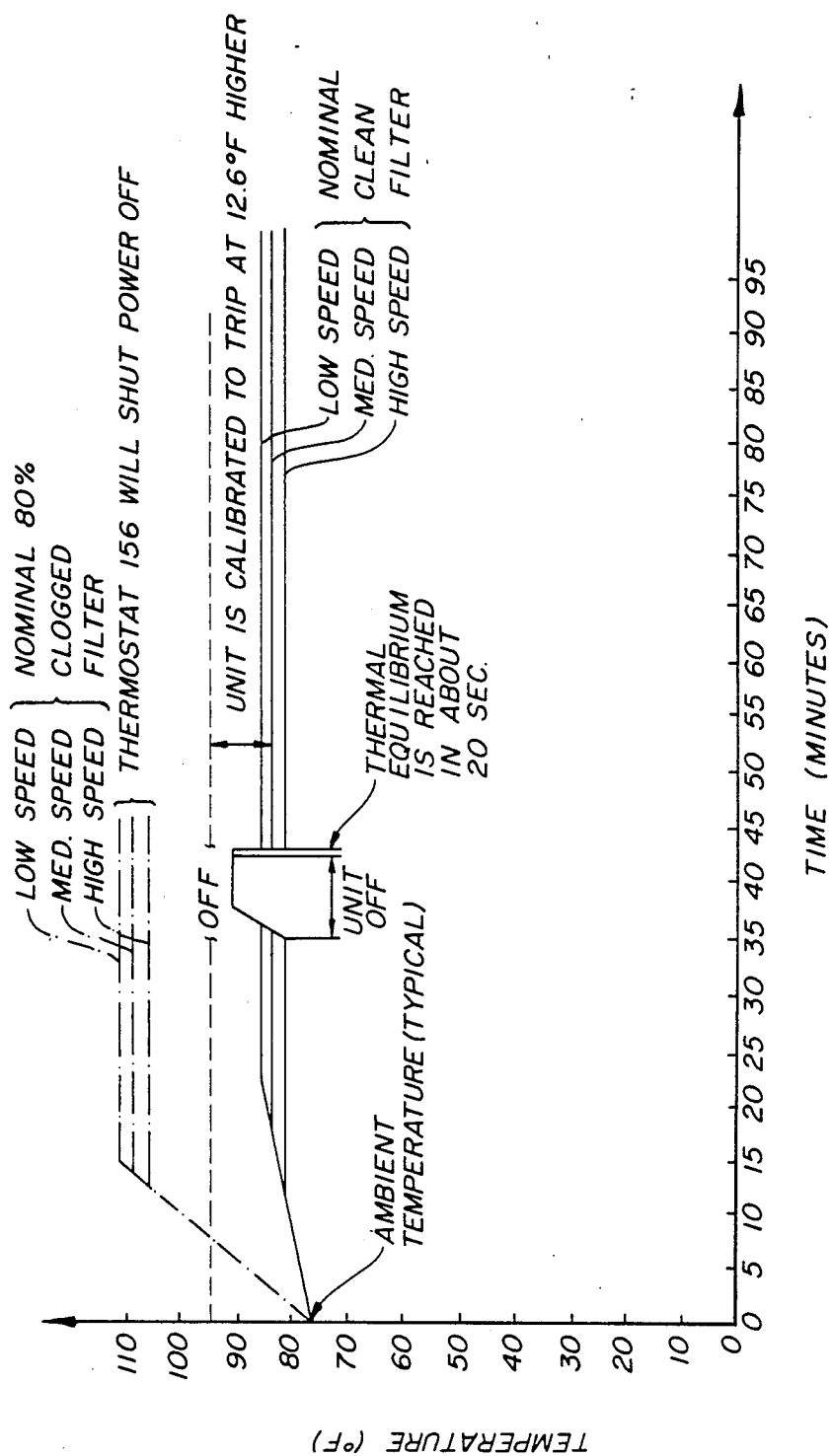

4,701,193

SMOKE EVACUATOR SYSTEM FOR USE IN LASER SURGERY

THE FIELD OF THE INVENTION

This invention relates to an apparatus for filtering the undesired by-products of laser surgery from a surgical site and more particularly to an apparatus which has an automatic indicator for notifying the user when the filter is clogged and in need of replacement.

BACKGROUND OF THE INVENTION

Related Applications

The present application relates to a smoke evacuator system for laser surgery. Two other applications are being filed simultaneously and are assigned to the same assignee as the present application: the first relating to a filter used with the system; and, the second relating to electronic circuitry for the system.

Laser surgery is becoming a more common as surgical modality with a large variety of uses. When a tissue is subjected to a high energy laser beam the tissue is vaporized. It is desirable to remove the vapor and other by-products from the surgical site in a controlled manner. The word smoke is intended to mean the by-products of laser surgery which are primarily gases, but can include some small amounts of liquid and solid particulate matter. The most common means of removing the vapor and other by-products is to use a suction tube at the surgical site to establish a flow of air which is then delivered to a filter placed in a housing with the motors and pumps that establish the vacuum flow. Present day vacuum apparatus usually works satisfactorily but are often heavy, difficult to move, noisy and expensive. Many present day vacuum apparatus do not have variable suction levels.

Many present day filter systems are difficult to replace when they become clogged. Certain filter systems do not have automatic warning systems to indicate that a filter is clogged.

Existing systems for monitoring the conditions of a filter usually attempt to monitor air flow rate through the filter or pressure drop across the filter. Although these systems work satisfactorily they tend to be expensive, complex and hard to calibrate and maintain in a surgical environment.

It would be desirable to have a light-weight, portable, quiet, powerful and inexpensive evacuator system for laser surgery which would include an easily replaceable filter and an automatic indicator of a clogged filter condition.

SUMMARY OF THE INVENTION

The present invention provides such an evacuator system for laser surgery which includes a replaceable filter and an automatic indicator of a clogged filter condition. The apparatus includes a housing which defines a first chamber with an inlet and a outlet. A fitting is attached to the inlet of the first chamber and the fitting defines a second chamber between the fitting inlet and outlet. A filter is removably place at the fitting inlet. An apparatus is provided for maintaining a negative pressure in the first chamber and thus establishing an airflow through the filter, the fitting and the first chamber to deliver laser surgery by-products to the filter with the flow of air so that the filter may trap and remove laser surgery by-products from the flow. A temperature sensing means is mounted in the second chamber for measuring the temperature of the airflow in the second chamber and for generating a signal indicative of the clogged condition of the filter. We have recognized that the temperature of the airflow in the second chamber is a good indicator of the clogged condition of the filter and thus can determine the clogged condition of the filter by making a simple temperature measurement.

A filter receptacle is usually attached about the fitting for receiving and removably holding the filter.

It is desirable to mount the fitting and the first chamber housing close together on a common mounting plate and then to place the entire apparatus within a case mounted on wheels and acoustically insulated. An exhaust muffler may be provided to reduce exhaust noise. The geometry of the fitting is preferably cylindrical with a converging section from the inlet to the mid portion of the fitting. This converging section maintains a desired flow rate so that the by-products entrained in the airflow will be properly disposed in the filter and will be less likely to float free into the environment.

A temperature sensor operates a warning light to indicate the clogged condition of the filter and is preferably a thermocouple.

A negative pressure is established in the first chamber by a centrifugal pump preferably driven by an electric motor. Speed control for the motor is preferably provided by using an AC motor controlled by a phase controller. The motor is cooled by air drawn into the case through an intake duct and circulated about the motor. The phase controller for the motor is preferably located in the vicinity of the air intake to facilitate the dissipation of heat developed in the phase controller. Alternatively, a vacuum line can be used to establish the negative pressure in the first chamber and a valve can be used to vary the pressure in the chamber.

A thermostat may be used to shut off the motor to provide protection from overheating if the temperature controller senses a clogged filter condition for an extended period of time, and temperature buildup occurs. The thermostat resets itself when the temperature cools down to approximately 20° F. below the trip point.

These and other features and advantages of the present invention will become apparent from the following detailed description of the preferred embodiments taken in conjunction with the following drawings:

DESCRIPTION OF THE DRAWINGS

FIG. 6 shows a chart illustrating features of the present invention.

DETAILED DESCRIPTION OF THE PREFERRED EMBODIMENTS

Figure 1:
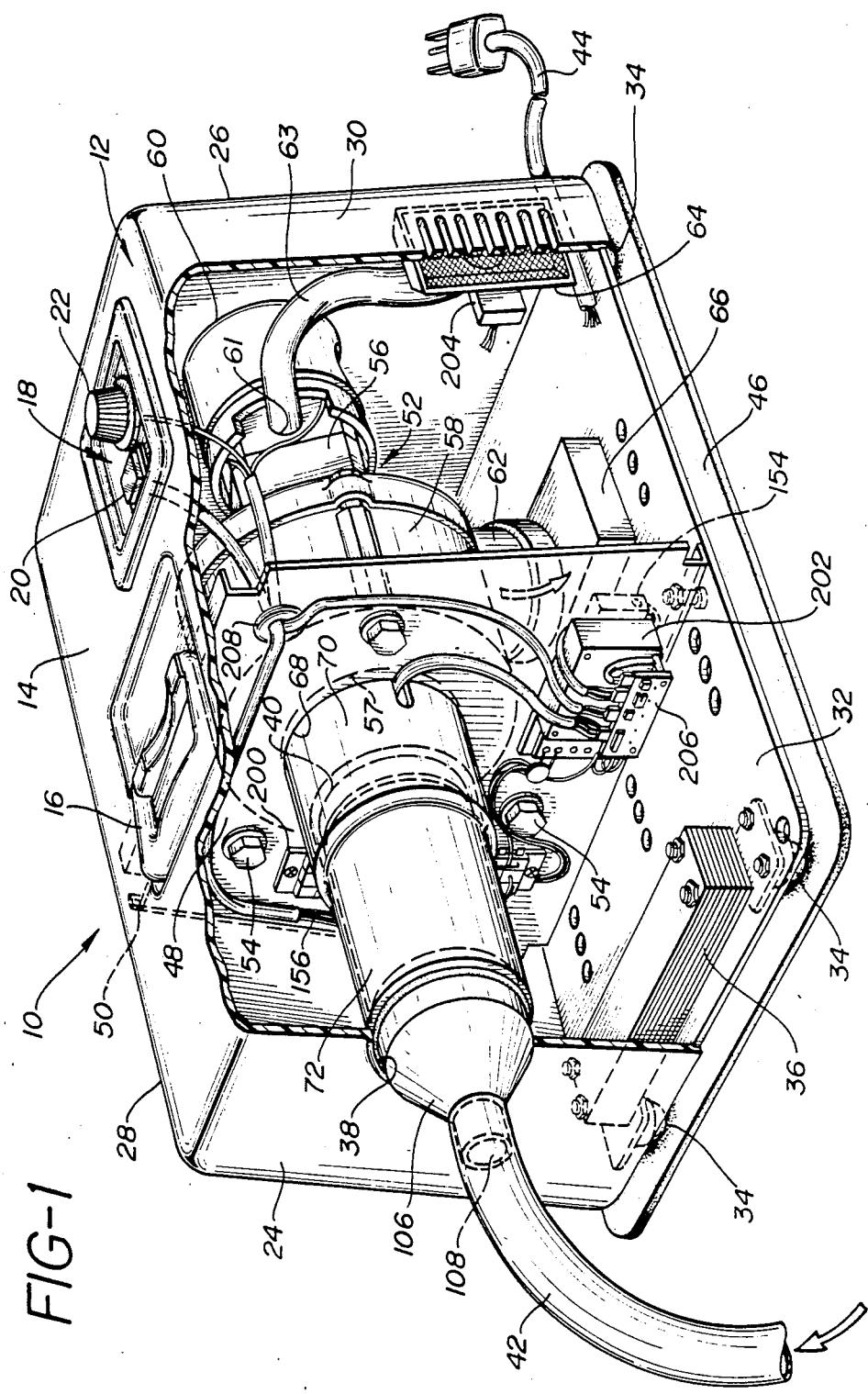
FIG. 1 shows a perspective view partly in section of the evacuator system of the present invention.

Referring the now to FIG. 1 there is shown a perspective view partly in section of the apparatus of the present invention.

The evacuator system 10 of the present invention is housed in a casing 12 having a top surface 14 on which a handle 16 and a control panel 18 are mounted. Control panel 18 has a warning light to 20 to indicate a clogged filter condition and a control knob 22 for controlling the amount of suction provided by the apparatus. Casing 12 also includes a front surface 24, back surface 26 and sides 28 and 30. In the preferred embodiment, top 14, front 24, back 26 and sides 28 and 30 are all integraly formed of a high strength light-weight plastic material. A separate bottom panel 32 is removably affixed to casing 12 to provide an enclosure within casing 12. Wheels 34 are supported on bottom panel 32 for portability and counter weights 36 are used to balance the interior components.

Front surface 24 has a circular opening 38 therein through which filter 40 may be inserted into case 12. A suction tube 42 connects to filter 40 and has a convenient length for extending to the surgical site. An electrical power cord 44 provides power to the internal components of the system.

The interior of casing 12 is filled with sections of acoustical insulation (not shown) to reduce noise generated by the apparatus. There are various openings in the casing and the bottom panel for air vents and access openings for the components inside casing 12 which will be discussed later in the application. Casing 12 also rests on a special mat 46 to keep the wheels from rolling and to reduce noise.

Still referring to FIG. 1 there are shown certain interior components of the system. A mounting plate 48 fits in grooves 50 on the interior of top 14 and sides 28 and 30. A centrifugal vacuum pump 52 is mounted by means of bolts 54 to mounting plate 48.

Vacuum pump 52 includes an alternating current single phase motor 56, an impeller chamber 58, an exhaust horn 62, and optional exhaust muffler 66 mounted on bottom panel 32 to reduce exhaust noise. Impeller blades (not shown) are mounted on the shaft (not shown) of motor 56 and rotate within impeller chamber 58 to create a negative pressure in chamber 58.

The inlet 57 to impeller chamber 58 is a generally circular opening aligned coaxially with a circular opening 68 in mounting plate 48. Exhaust horn 62 from impeller chamber 58 extends tangentially from generally cylindrical impeller chamber 58 so that the airflow exits impeller chamber 58 without impinging upon the electrical windings of motor 56. As an alternative feature an exhaust pipe (not shown) may be connected to exhaust horn 62 and exit through an appropriate opening in casing 12 to connect with the normal exhaust in the operating room.

A cooling fan 59 (see FIG. 2) is mounted in the vicinity of the electrical windings of motor 56 and covered by a liquid sealed cap 60 having an intake port 61 which connects to an intake pipe 63 which in turn connects to an intake manifold 64 mounted on the inside of casing 12 in the vicinity of intake vents conveniently locate through casing 12.

Figure 2:
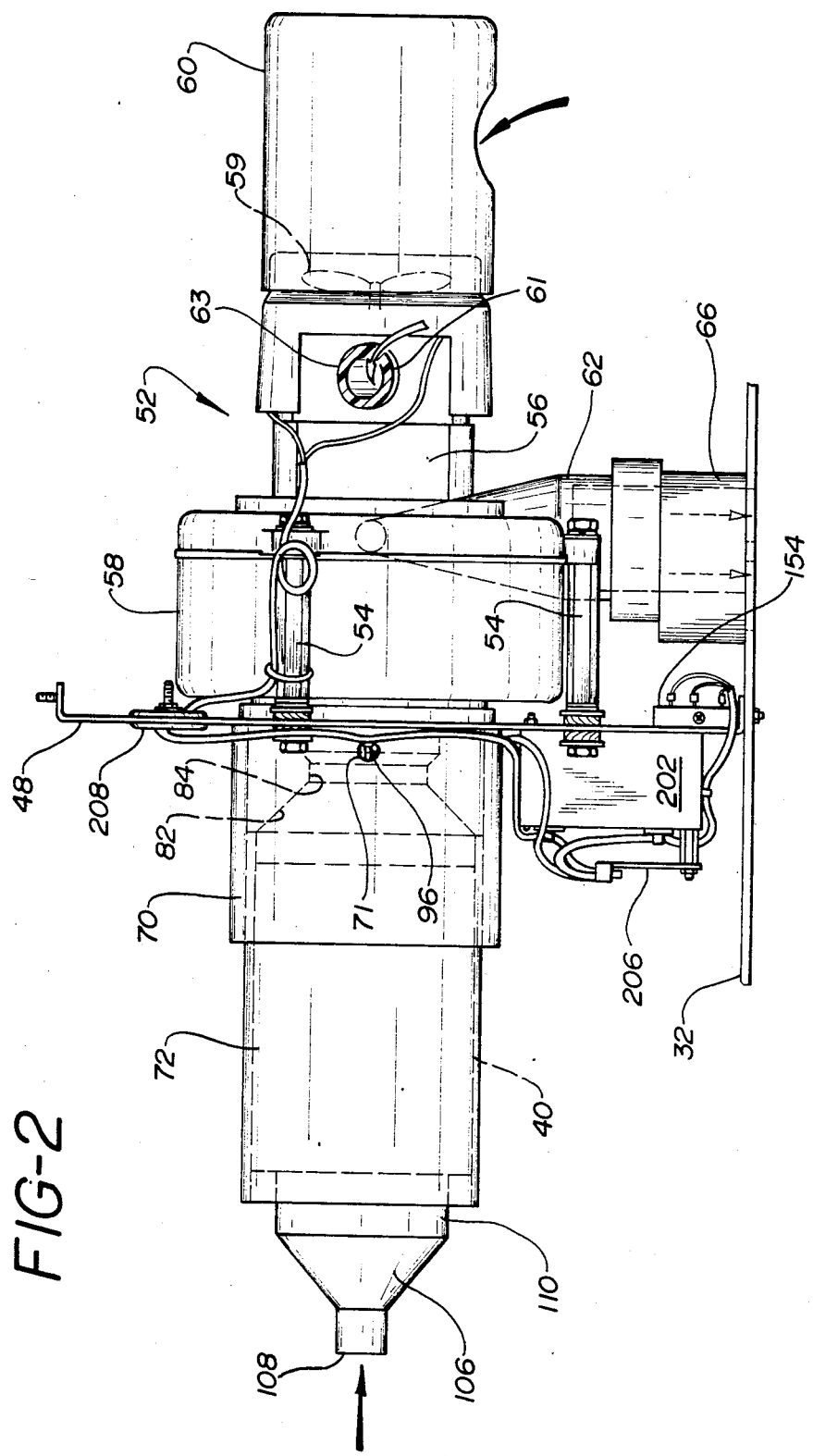
FIG. 2 shows a side elevation of key components of the apparatus of FIG. 1.

Referring now to FIG. 2 there is shown a filter collar 70 and filter duct 72, which are disposed on the opposite side of mounting plate 48 from vacuum pump 52 and aligned generally coaxially with vacuum pump 52. Filter duct 72 fits flush with opening 38 in the front wall 24 of casing 12 and receives filter 40. It is preferred that filter duct 72 be bonded to the peripheral surface of opening 38 to reduce vibration.

Figure 3:
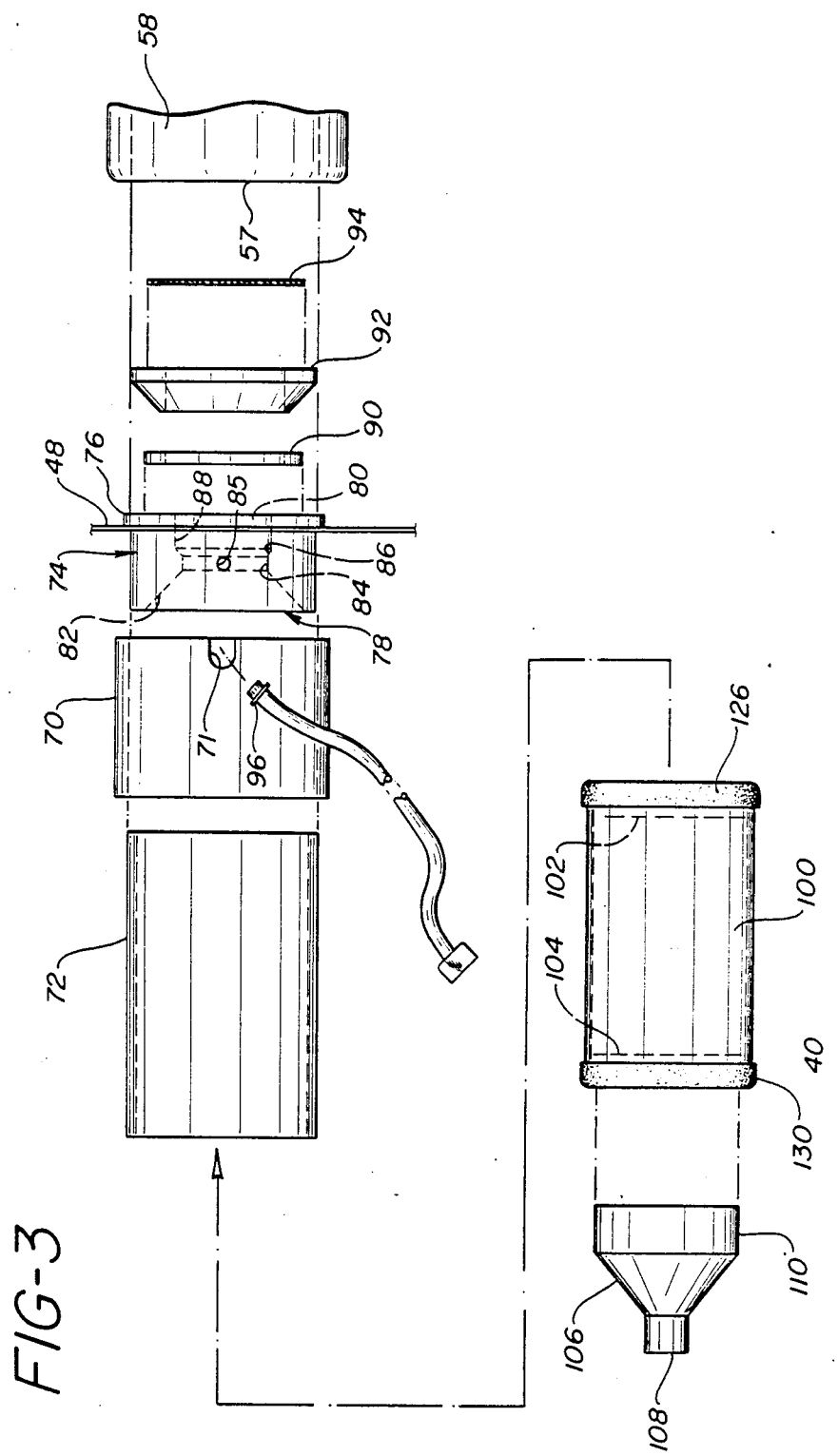
FIG. 3 shows a detailed exploded perspective view of a portion of the components shown in FIG. 2.
Figure 4:
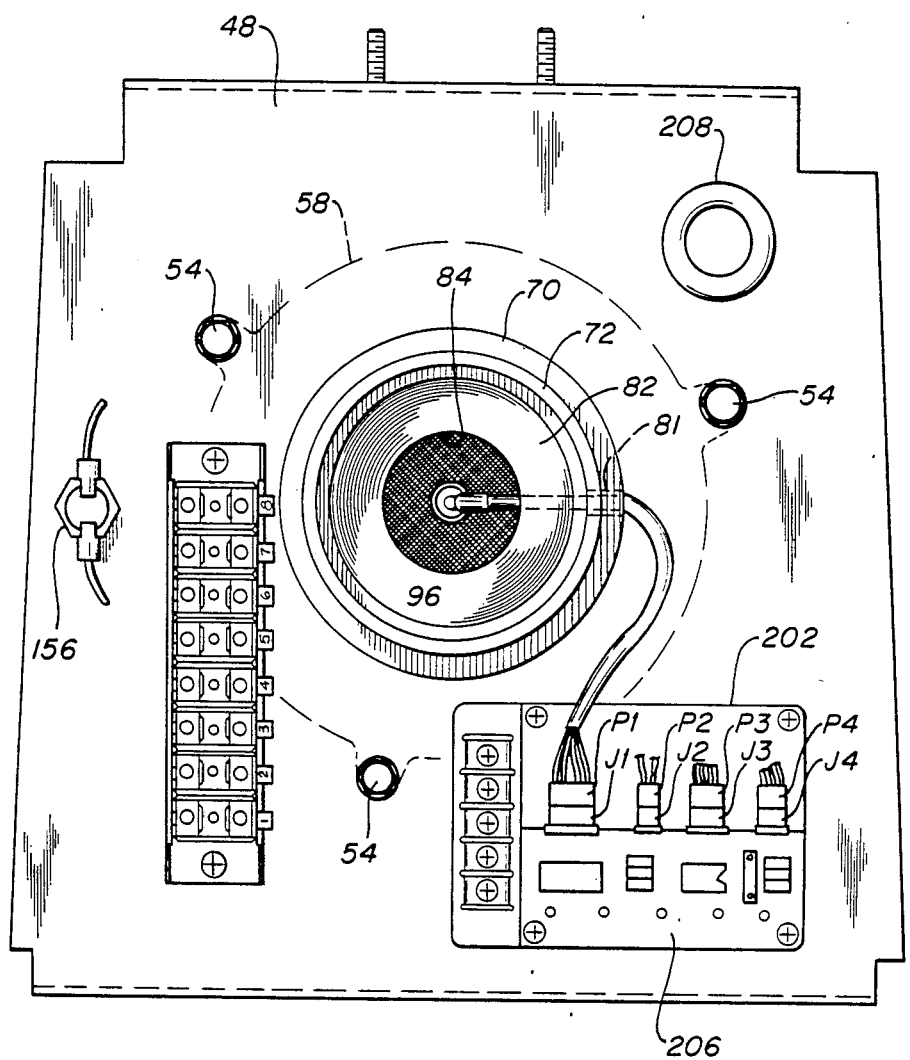
FIG. 4 shows an end view of the components shown in FIG. 2.

Referring now to FIG. 3 the details of the filter receptacle assembly will be discussed. A generally cylindrical fitting 74 having a radially outwardly extending flange 76 is inserted through opening 68 in mounting plate 48 and bonded in place. In the preferred embodiment, fitting 74 defines a generally cylindrical passage extending from the inlet 78 to outlet 80 of fitting 74 which has a converging section 82 of decreasing diameter extending from inlet 78 to an interior chamber 84 of constant diameter which joins a slightly diverging section 86 and then a further section 88 of constant diameter extending to outlet 80.

Flange 76 supports gaskets 90 and 92 and metal screen 94 for providing a sealed fluid communication with inlet 57 to impeller chamber 58. When motor 56 and correspondingly impeller chamber 58 which is attached to motor 56 is bolted to mounting plate 48 by means of bolts 54 gaskets 90 and 92 form a tight seal with fittings 74. Screen 94 prevents solid material from entering into impeller chamber 58.

The diameter of filter duct 72 is such that filter 40 slides conveniently within filter duct 72. Filter 40 is held in place only by the vacuum provided within the system and has no locks or mechanical retainers. Thus, filter 40 may easily removed from filter duct 72 when it becomes clogged by merely turning off the vacuum pump 52. Suction tube 42 extends from inlet 108 of cone 106 to the operative site. It will appreciated that filter 40 is conveniently removable and completely disposable.

Still referring to FIG. 3 it can be seen that filter collar 70 has a slot 71 at one end and fitting 74 has a hole 85 through its side to permit access to chamber 84.

A temperature controller 96 is mounted through slot 71 and hole 85 and extends into chamber 84. It is not critical that the temperature sensing device be exactly in chamber 84 but can be anywhere within fitting 74. Temperature controller 96 monitors the temperature downstream of filter 40 and upstream of impeller chamber 58. A variety of devices can be used as temperature sensors including thermocouples or thermisters or other suitable temperature sensors well-known in the art. Temperature controller 96 is connected to suitable electronic circuitry disposed within casing 12 for generating a signal to activate a warning light or bell when filter 40 becomes clogged.

This electronic circuitry will be discussed in general in connection with the block diagram shown in FIG. 5 in this application and will be discussed more particularly in a co-pending application Ser. No. 774,693, filed on the same date as this application and assigned to the assignee of the present application now U.S. Pat. No. 4,642,128 issued Feb. 10, 1987. The correlation between the temperature sensed by temperature controller 96 and the clogged condition of the filter will be discussed later in this application in connection with FIG. 6.

Figure 5:
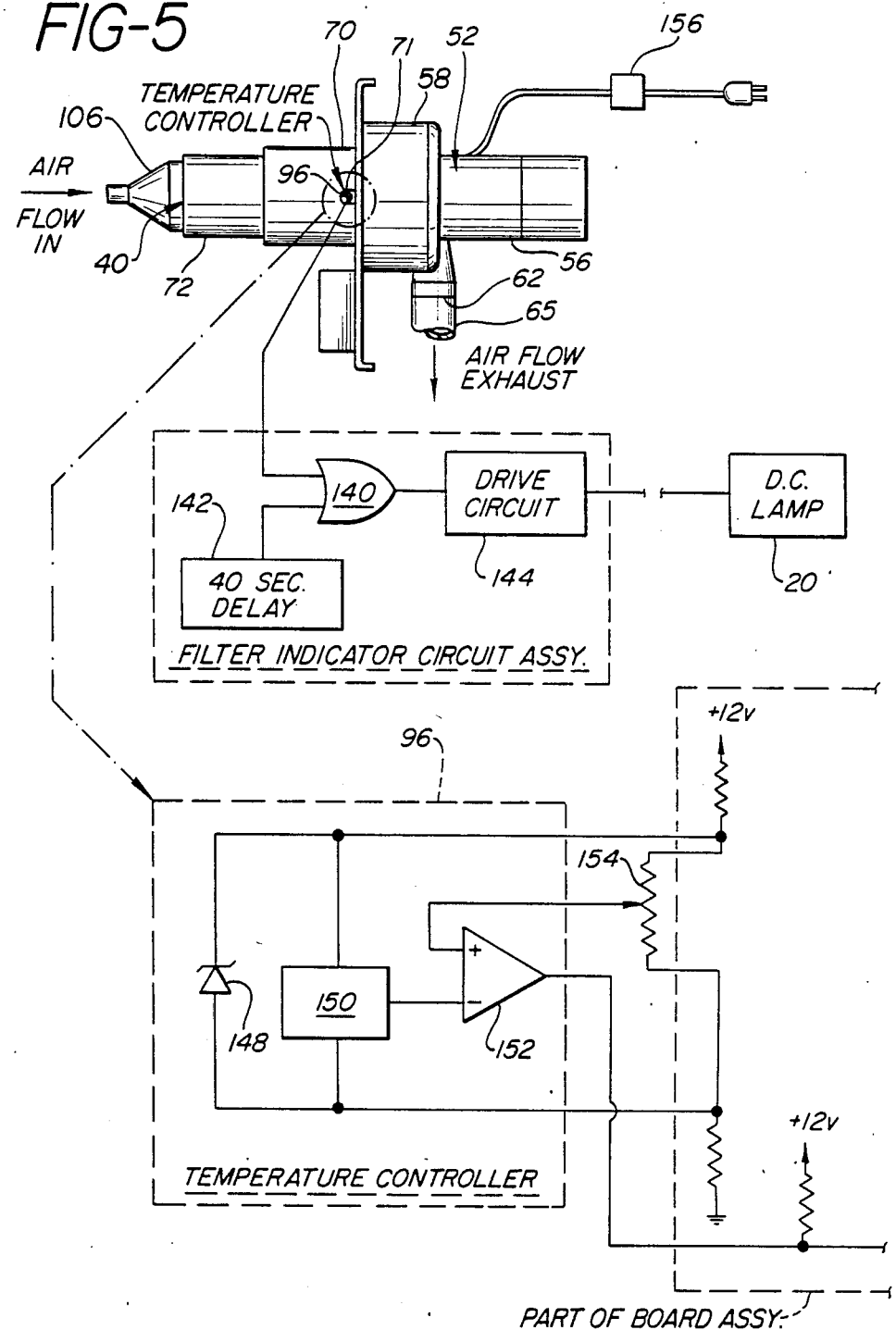
FIG. 5 shows a blocked diagram of the electrical circuitry for the apparatus of FIG. 1.

Referring now to FIG. 5, temperature controller 96 generates a signal indicative of the temperature within fitting 74 and transmits that signal to an OR gate 140. A temperature delay circuit 142 has a built in nominal forty second delay to cause the circuit to ignore temperature reading for a forty seconds lapse of time every time one turns the unit on. This eliminates false indications due to internal temperature increases immediately after the system is turned on. If the signal delivered to OR gate 140 by either temperature sensor 96 or time delay circuit 142 is high then the output of OR gate 140 remains high and keeps drive circuit 144 turned off and correspondingly keeps the warning device (which in the preferred embodiment is a light 20 but may also be an audible alarm) turned off.

The time delay circuit is typically a type 555 integrated circuit monostable multi-vibrator in which the resistance and capacitive levels are chosen to set the desired time constant.

The temperature controller circuit 96 is shown also in FIG. 5 and includes a Zener diode 148 a sensor preferably a thermocouple 150, a comparator 152 is typically a type LM-3911 temperature controller chip where reference voltage is provided by the Zener diode 148 and a trip voltage is set on the potentiometer 154 so that when the output of thermocouple 150 reaches the trip voltage the output of temperature controller circuit 96 goes low. If time delay circuit 142 is also low the output of OR gate 140 will go low and turn on lamp 20 through drive circuit 144.

The thermostat 156 is mounted on mounting plate 48 and connected between the source of electrical power and motor 56 to turn off the power and thus motor 56 in response to an overheat condition. Thermostat 156 is mounted on mounting plate 48 because that is one of the warmer spots within casing 12. Thermostat 156 shuts off the power if a clogged filter condition exists for an extended period of time, or if overheating occurs for any other reason.

Referring now to FIG. 6, the correlation between the temperature monitored by temperature controller 96 and the clogged condition of filter 40 will now be discussed. Control knob 22 operates a phase control system to control the speed of motor 56 at low, medium or high or it may be used for an infinitely variable phase control motor between upper and lower limits. With a clean filter the operating temperature of temperature controller 96 is shown for a low, medium and high speed on the chart shown in FIG. 6. As the filter becomes clogged the airflow through the system diminshes and the temperature of chamber 84 within fitting 74 begins to rise. The electronic circuitry is set by means of potentiometer 154 to trip at a prescribed temperature rise to initiate a warning signal either by way of a light 20 or an audible alarm (not shown).

The operating temperature of the system with a filter which is approximately 80 percent clogged is also shown on FIG. 6. The system will not operate indefinitely at this high temperature level but will be shut off by thermostat 156. In the present design, the thermostat 156 shuts off the power after about thirty minutes of operation with a clogged filter. It is anticipated, however, that the user will note that alarm signal and change the filter long before thermostat 156 shuts the system off.

The operation of the system will now be described. The operation of this system depends on the realization that the temperature in chamber 84 within fitting 74 will increase in a predictable fashion as the filter becomes clogged and the airflow through fitting 74 reduces.

A clean filter 40 is placed in filter duct 72 and the system is energized so that motor 56 will turn on and start the impellers rotating inside impeller chamber 58 to develop a vacuum inside impeller chamber 58. Air enters the system through filter cone 106 through duct 72 and fitting 74 past temperature controller 96 into inlet 57 to impeller chamber 58 circulates through impeller chamber 58 with the aid of impellers (not shown) and exits through exhaust horn 62 either into the interior of casing 12 or optionally through muffler 66 and exhaust openings in case 12 to the atmosphere.

A cooling fan 59 draws air through intake manifold 64, intake pipe 63, endcaps 60 about motor 56 to cool motor 56. The cooling air drawn in by cooling fan 59 is exhausted into the interior of the cabinet and out through suitable exhaust ports in bottom panel 32.

When filter 40 becomes clogged the airflow through fitting 74 decreases and the temperature rises. This increase in temperature is sensed by temperature controller 96 which operates the previously described electronic circuitry to provide an alarm signal either by way of light 20 or an audible alarm. The system will operate with an 80 percent clogged filter for approximately thirty minutes before thermostat 156 turns the power to motor 56 off and shuts down the system. It is anticipated that a user will note the alarm signal and change the filter 40 long before thermostat 156 turns the system off.

Filter 40 is held firmly in place by the vacuum when the system is on. When the system is in operation tugging and pulling on suction tube 42 will not remove or loosen filter 40 from its position in filter duct 72 and will not affect the operation of the system. When one wishes to change the filter one merely turns off the power to dissipate the vacuum and then filter 40 is easily removable from filter duct 72 within a matter of a few seconds. The system may then be turned on again, and after the time delay has expired, the system is ready to fully operate again. The delay only disables the alarm circuit.

Referring again to FIG. 2 it is noted that there is a converging section 82 at the inlet of fitting 74. This converging section increases the airflow through filter 40 so that the laser surgery by-products which are principally gaseous are trapped in the filter. If the airflow is too slow not all of these by-products will be trapped by the filter and the by-product gases may begin to disseminate into the surrounding environment.

It can be seen that the present invention provides a disposable, readily removable filter for a laser surgery smoke evacuation system.

Prior art evacuator systems did not arrange the motor and the filter in a direct line but separated them with a large cavity and distance which produces leakage, reduction in air suction and need for a more powerful motor to achieve a given level of suction, elaborate airseals and structural supports are needed to hold everything in place with prior art devices. By placing the motor and the filter in line and close together it became possible to monitor the clogged condition of the filter by simply sensing the temperature in the chamber provided by fitting 74. This inline design of the motor and filter makes it possible to quickly and easily change the filter in a few seconds.

The present invention has been described in conjunction with certain preferred embodiments. Those skilled in the art will appreciate that many modifications and changes may be made to the preferred embodiments without departing from the spirit of the present invention. It is therefor, not intended to limit the present invention except to set forth in the following claims.

We claim:

1. An apparatus for removing by-products of laser surgery from the surgical site comprising:
    a housing defining a first chamber having an inlet and an outlet;
    a fitting attached to and provising fluid communication into said first chamber, said fitting having an inlet and an outlet and defining a second chamber between said inlet and said outlet;

a filter removably disposed at said fitting inlet and having and inlet and an outlet;

means for maintaining a negative pressure within said first chamber and thus establishing a flow of air through said filter, said fitting and said first chamber to deliver laser surgery by-products to said filter with the flow of air so that said filter may trap and remove laser surgery by-products from the flow;

temperature sensing means disposed in said second chamber for measuring the temperature of air in said second chamber and for generating a signal indicative of a clogged condition of said filter; and a common mounting plate for said fitting and said housing said common mounting plate having a first and second opposed sides said fitting extending from said first side of said mounting plate and said housing extending from said second side of said mounting plate; and said second chamber defined by said fitting including a generally cylindrical cross section, said cross section converging from said fitting inlet to the vicinity of said temperature sensing mens and then remaining at a constant diameter from the vicinity of said temperature sensing means to said fitting outlet.

2. The apparatus of claim 1 further including a filter receptacle attached to said fitting and in fluid communication with said fitting inlet, said filter being removably disposed in said filter receptacle.

3. The apparatus of claim 1 further including means removably connected to said filter inlet extending to the vicinity of the surgical site.

4. The apparatus of claim 1 further including means for varying the flow rate of said air flow means.

5. The apparatus in claim 1 further including a muffler in fluid communication with said first chamber outlet for reducing exhaust noise.

6. The apparatus in claim 1 wherein said signal generated by said temperature sensing means operates a warning light to indicate a clogged filter condition.

7. The apparatus in claim 1 wherein said temperature sensing means includes a thermocouple.

8. The apparatus in claim 1 wherein the means for maintaining a negative pressure includes a vacuum line fitting disposed about the outlet of said first chamber;

a vacuum line removably connectable to said vacuum fitting; and, further including valve means for varying the pressure in said first chamber.

9. The apparatus of claim 1 wherein the means for maintaining a negative pressure includes a centrifugal pump having impeller means mounted in said first chamber;

an electric motor operatively connected to said impeller means for driving said impeller means within said first chamber; and, further including motor control means for varying the output of said motor to vary the rotational velocity of said impeller means.

10. The apparatus of claim 1 further including means for shutting off said negative pressure maintaining means in response to a predetermined temperature increase sensed by said temperature sensing means.

11. The apparatus of claim 10 wherein said shut-off means includes a thermostat.

12. The apparatus of claim 13 further including means for cooling said electric motor including an air intake duct for delivery ambient air to said motor and means for circulating said ambient air about said motor.

13. The apparatus of claim 12 wherein said motor is a single phase motor and said means for controlling the output of said motor is a phase controller, said phase controller being disposed in the vicinity of said air intake duct inlet to facilitate the dissipation of heat developed in the phase controller when the motor is operated at low speeds.

14. The apparatus in claim 1 further including a casing within which said first chamber, said fitting, said filter and said temperature sensing means may be enclosed;

said casing including a base; and, a plurality of wheels mounted to the said base to facilitate the portability of said apparatus.

15. The apparatus in claim 14 further including acoustical sound insulation within said casing and substantially surrounding said fitting and said first chamber.

* * * * *